United States Patent [19]
Agrawal et al.

[11] Patent Number: 5,968,909
[45] Date of Patent: Oct. 19, 1999

[54] METHOD OF MODULATING GENE EXPRESSION WITH REDUCED IMMUNOSTIMULATORY RESPONSE

[75] Inventors: Sudhir Agrawal, Shrewsbury; Jamal Temsamani; Qiuyan Zhao, both of Worcester, all of Mass.

[73] Assignee: Hybridon, Inc., Milford, Mass.

[21] Appl. No.: 08/511,536

[22] Filed: Aug. 4, 1995

[51] Int. Cl.$^6$ .......................... A61K 31/70; C07H 21/00
[52] U.S. Cl. .............................................. 514/44; 536/24.5
[58] Field of Search ............................ 514/44; 536/23.1, 536/24.5, 22.1

[56] References Cited

U.S. PATENT DOCUMENTS 5,663,153  9/1997  Hutcherson et al. ................... 514/44

OTHER PUBLICATIONS

Concise Encyclopedia Chemistry, M. Eagleson trans. Walter de Gruyter, New York. p. 741, 1994.
Stein et al. Science 261: 1004–1012, Aug. 1993.
Mojcik et al. Clinical Immunol. Immunopath. 67: 130–136, May 1993.
Branda et al. Biochem. Pharmacol. 45: 2037–2043, Oct. 1993.
Goodchild. Bioconjugate Chem. 1(3): 165–187, 1990.
McIntrye et al. Antisense Res. Dev. 3:309–322, 1993.
Messina et al. Cell Immunol. 147: 148–157, 1993.
Kreig et al. Nature 374: 546–549, 1995.
Pisetsky et al. (1993) *Life Sciences* 54:101–107.
Kuramoto et al. (1992) *Jpn. J. Cancer Res.* 83:1128–1131.
Stein et al. (1993) *Science* 261:1004–1012.
Branda et al. (1993) *Biochem. Pharm.* 45:2037–2043.
Lisziewicz et al. (1994) *Proc. Natl. Acad. Sci. USA* 91:7942–7946.
Bayever et al. (1993) *Antisense Res. Dev.* 3:383–390.
Benbernou et al. (1993) *Biochimie* 75:55–61.
Yamamoto et al. (1992) *J. Immunol.* 148:4072–4076.
Mojcik et al. (1993) *Clin. Immunol. and Immunopat.* 67:130–136.
Tanaka et al. (1992) *J. Exper. Medicine* 175:597–607.
Horwitz et al. (1992) *J. Virol.* 66:2170–2179.
Zhao et al. (1986) *Biochemical Pharmacology* 51:173–182.
Pisetsky et al. (1993) *Molecular Biology Reports* 18:217–221.
Zhou et al. (1994) *Nucleic Acids Research* 22:453–456.

*Primary Examiner*—George C. Elliott
*Assistant Examiner*—Thomas G. Larson
*Attorney, Agent, or Firm*—Hale and Dorr LLP

[57] ABSTRACT

The present invention provides a method of reducing the immunostimulatory effects of certain phosphorothioate oligonucleotides used to treat pathogen-mediated disease states and other medical conditions. Immunostimulatory effects of phosphorothioate oligonucleotides are reduced in accordance with the method of the invention by modifying at least one chemical structure within the phosphorothioate oligonucleotide to produce an immunostimulatory response-reducing phosphorothioate oligonucleotide, which is then administered to a mammal afflicted with the disease or condition being treated. The immune response of the mammal is also monitored in the method of the invention.

19 Claims, 6 Drawing Sheets

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "phosphorothioate linked
           deoxyribonucleic acid"

(iv) ANTI-SENSE: YES (vi) ORIGINAL SOURCE:
       (A) ORGANISM: Human immunodeficiency virus type 1 gag gene (ix) FEATURE:
       (A) NAME/KEY: misc_feature
       (B) LOCATION: 1..25
       (D) OTHER INFORMATION: /product= "phosphorothioate
           linkage"

(xi) SEQUENCE DESCRIPTION: SEQ ID NO:1:

CTCTCGCACC CATCTCTCTC CTTCT                                           25

(2) INFORMATION FOR SEQ ID NO:2:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "chimeric
           methylphosphonate/phosphorothioate linked
           deoxyribonucleic acid"

(iv) ANTI-SENSE: YES (vi) ORIGINAL SOURCE:
       (A) ORGANISM: Human immunodeficiency virus type 1 gag gene (ix) FEATURE:
       (A) NAME/KEY: misc_feature
       (B) LOCATION: 1..5
       (D) OTHER INFORMATION: /product= "methylphosphonate
           linkage"

(ix) FEATURE:
       (A) NAME/KEY: misc_feature
       (B) LOCATION: 6..20
       (D) OTHER INFORMATION: /product= "phosphorothioate
           linkage"

(ix) FEATURE:
       (A) NAME/KEY: misc_feature
       (B) LOCATION: 21..25
       (D) OTHER INFORMATION: /product= "methylphosphonate
           linkage"

(xi) SEQUENCE DESCRIPTION: SEQ ID NO:2:

CTCTCGCACC CATCTCTCTC CTTCT                                           25

(2) INFORMATION FOR SEQ ID NO:3:

(i) SEQUENCE CHARACTERISTICS:

(A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "hybrid phosphorothioate
            linked ribonucleic/deoxyribonucleic acid"

(iv) ANTI-SENSE: YES (vi) ORIGINAL SOURCE:
        (A) ORGANISM: Human immunodeficiency virus type 1 gag gene (xi) SEQUENCE DESCRIPTION: SEQ ID NO:3:

CUCUCGCACC CATCTCTCTC CUUCU                                             25

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: both
        (D) TOPOLOGY: both (ii) MOLECULE TYPE: other nucleic acid
        (A) DESCRIPTION: /desc = "looped phosphorothioate
            linked deoxyribonucleic acid"

(iv) ANTI-SENSE: YES (vi) ORIGINAL SOURCE:
        (A) ORGANISM: Human immunodeficiency virus type 1 gag gene (ix) FEATURE:
        (A) NAME/KEY: stem_loop
        (B) LOCATION: 22..33

(ix) FEATURE:
        (A) NAME/KEY: misc_feature
        (B) LOCATION: 1..33
        (D) OTHER INFORMATION: /product= "phosphorothioate
            linkage"

(xi) SEQUENCE DESCRIPTION: SEQ ID NO:4:

CTCTCGCACC CATCTCTCTC CTTCTGGAGA GAG                                    33

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate linked
            deoxyribonucleic acid"

(iv) ANTI-SENSE: YES (vi) ORIGINAL SOURCE:
        (A) ORGANISM: Human immunodeficiency virus type 1 rev gene (ix) FEATURE:
        (A) NAME/KEY: misc_feature
        (B) LOCATION: 1..27
        (D) OTHER INFORMATION: /product= "phosphorothioate
            linkage"

(xi) SEQUENCE DESCRIPTION: SEQ ID NO:5:

TCGTCGCTGT CTCCGCTTCT TCTTGCC                                           27

(2) INFORMATION FOR SEQ ID NO:6:

```
    (i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "chimeric
            methylphosphonate/phosphorothioate linked
            deoxyribonucleic acid"

(iv) ANTI-SENSE: YES (vi) ORIGINAL SOURCE:
        (A) ORGANISM: Human immunodeficiency virus type 1 rev gene (ix) FEATURE:
        (A) NAME/KEY: misc_feature
        (B) LOCATION: 1..5
        (D) OTHER INFORMATION: /product= "methylphosphonate
            linkage"

(ix) FEATURE:
        (A) NAME/KEY: misc_feature
        (B) LOCATION: 6..22
        (D) OTHER INFORMATION: /product= "phosphorothioate
            linkage"

(ix) FEATURE:
        (A) NAME/KEY: misc_feature
        (B) LOCATION: 23..27
        (D) OTHER INFORMATION: /product= "methylphosphonate
            linkage"

(xi) SEQUENCE DESCRIPTION: SEQ ID NO:6:

TCGTCGCTGT CTCCGCTTCT TCTTGCC                                            27

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "hybrid phosphorothioate
            linked ribonucleic/deoxyribonucleic acid"

(iv) ANTI-SENSE: YES (vi) ORIGINAL SOURCE:
        (A) ORGANISM: Human immunodeficiency virus type 1 rev gene (ix) FEATURE:
        (A) NAME/KEY: misc_feature
        (B) LOCATION: 1..27
        (D) OTHER INFORMATION: /product= "phosphorothioate
            linkage"

(xi) SEQUENCE DESCRIPTION: SEQ ID NO:7:

UCGUCGCTGT CTCCGCTTCT TCTUGCC                                            27

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate linked
            deoxyribonucleic acid"
```

-continued

```
     (iv) ANTI-SENSE: YES (vi) ORIGINAL SOURCE:
          (A) ORGANISM: human p53

(ix) FEATURE:
          (A) NAME/KEY: misc_feature
          (B) LOCATION: 1..20
          (D) OTHER INFORMATION: /product= "phosphorothioate
              linkage"

(xi) SEQUENCE DESCRIPTION: SEQ ID NO:8:

CCCTGCTCCC CCCTGGCTCC                                                    20

(2) INFORMATION FOR SEQ ID NO:9:

(i) SEQUENCE CHARACTERISTICS:
          (A) LENGTH: 6 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "phosphorothioate linked
              deoxyribonucleic acid"

(iv) ANTI-SENSE: YES (ix) FEATURE:
          (A) NAME/KEY: misc_feature
          (B) LOCATION: 1..6
          (D) OTHER INFORMATION: /product= "phosphorothioate
              linkage"

(xi) SEQUENCE DESCRIPTION: SEQ ID NO:9:

CGCGCG                                                                    6

(2) INFORMATION FOR SEQ ID NO:10:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "phosphorothioate linked
              deoxyribonucleic acid"

(iv) ANTI-SENSE: YES (ix) FEATURE:
          (A) NAME/KEY: misc_feature
          (B) LOCATION: 1..10
          (D) OTHER INFORMATION: /product= "phosphorothioate
              linkage"

(xi) SEQUENCE DESCRIPTION: SEQ ID NO:10:

GACGATCGTC                                                               10
```

METHOD OF MODULATING GENE EXPRESSION WITH REDUCED IMMUNOSTIMULATORY RESPONSE

The present invention relates to the field of antisense pharmaceuticals, and more specifically to methods for reducing the immunostimulatory response which may be induced in treated individuals by such antisense pharmaceuticals.

BACKGROUND OF THE INVENTION

Antisense oligonucleotide technology presents an exciting new therapy for many diseases, including pathogenic infections, cancer, and inherited conditions. The field has progressed enormously over the past decade, and currently numerous clinical trials are in progress or are proposed. Antisense oligonucleotides act by binding to a target nucleic acid by Watson-Crick or Hoogstein base-pairing. Antisense oligonucleotides may be designed to target and to inhibit any single gene within an organism's genome. For example, the oligonucleotides of SEQ ID NO:1 and SEQ ID NO:5 are phosphorothioate oligonucleotides complementary to the gag and rev regions of HIV-1 which inhibit HIV-1 replication, and the phosphorothioate oligonucleotide of SEQ ID NO:8 binds to the human p53 oncogene. The antisense approach is currently the only known strategy that has broad potential for precise and effective modulation of the expression of specific genes in a disease situation.

However, some antisense oligonucleotides containing phosphorothioate linkages exhibit an immunostimulatory response, causing B cell proliferation and/or an antibody response both in vitro and in vivo. This immunostimulatory response is not characteristic of all antisense oligonucleotides containing phosphorothioate linkages. For example, it is known that the phosphorothioate oligonucleotide of SEQ ID NO:8 does not induce an immunostimulatory effect.

Phosphorothioate oligonucleotide immunostimulatory effects appear to be dependent on particular sequences within the oligonucleotide but remain independent of whether the oligonucleotide is antisense, sense, or scrambled with respect to the respective target gene. Some phosphorothioate oligonucleotides induce only cell proliferation, and other phosphorothioate oligonucleotides produce no immunostimulatory effect at all. McIntyre et al. (1993) *Antisense Res. Dev.* 3:309–322 discloses that certain oligonucleotides can cause pronounced splenomegaly in athymic nude mice. Messina et al. (1993) *Cell Immunol.* 147:148–157; and Pisetsky et al. (1994) *Life Sciences* 54:101–107 disclose that DNA as well as structurally related synthetic oligonucleotides and polynucleotides stimulate lymphocytes, but the mechanism for this stimulation is still not fully understood. B cells are usually activated from the resting state by antigen binding to surface immunoglobulin. In mice, activation can also be modulated by physiological mediators, such as interleukin-2 (IL-2), interleukin-4 (IL-4), γ-interferon, and non-physiological mitogens, such as lipopolysaccharide (LPS), Concanavalin A (con A), and pokeweed mitogen (PWM).

Certain sequence motifs or structures of oligonucleotides may play important roles in causing stimulation of murine cells. Kuramoto et al. (1992) *Jpn. J. Cancer Res.* 83:1128–1131 discloses that the presence of particular palindromic sequences including 5'-CG-3' motif(s) is a critical determinant in oligonucleotides for induction of natural killer cell activation and interferon production. Krieg et al. (1995) *Nature* 374:546–549 discloses that optimal B cell activation requires a DNA motif in which an unmethylated CpG dinucleotide is flanked by two 5'-purines and two 3'-pyrimidines.

Because of the continued need for specific treatments for diseases and inherited conditions, and the high level of specificity provided through use of antisense therapeutics capable of modulating the expression levels of targeted genes, a need exists for reducing the immunostimulatory response induced by certain phosphorothioate oligonucleotides.

SUMMARY OF THE INVENTION

The present inventors have discovered a method of reducing the immunostimulatory effects of certain phosphorothioate oligonucleotides by altering sequences or structures within those oligonucleotides, for example, by introducing non-phosphorothioate linkages into the oligonucleotide, by altering the degree of substitution with phosphorothioate internucleotide linkages in the oligonucleotide, by substituting ribonucleotides for some of the deoxyribonucleotides on the sugar backbone of the phosphorothioate oligonucleotide, and by removing immunogenic nucleotides from the phosphorothioate oligonucleotide. In accordance with the invention these alterations of sequences or structures within the phosphorothioate oligonucleotide are defined as "immunostimulatory response-reducing modifications".

In one embodiment, the invention provides a method of reducing an immunostimulatory response of a mammal to a phosphorothioate oligonucleotide which comprises the steps of modifying at least one chemical structure in the phosphorothioate oligonucleotide to produce an immunostimulatory response-reducing phosphorothioate oligonucleotide; administering a therapeutic formulation containing the immunostimulatory response-reducing phosphorothioate oligonucleotide to the mammal; and monitoring the immune response of the mammal.

BRIEF DESCRIPTION OF THE DRAWINGS

The various features of the invention may be more fully understood from the following description when read together with the accompanying drawings.

DETAILED DESCRIPTION OF THE PREFERRED EMBODIMENTS

The patent and scientific literature referred to herein establishes the knowledge that is available to those with skill in the art. The issued U.S. patent and allowed applications cited herein are hereby incorporated by reference.

In accordance with the method of the invention, an immunostimulatory response induced by a phosphorothioate oligonucleotide is modified by introducing an immunostimulatory response-reducing modification into the sequence or the structure of the oligonucleotide. In the first step of the method of the invention, at least one chemical structure in the phosphorothioate oligonucleotide is modified to produce an immunostimulatory response-reducing phosphorothioate oligonucleotide. In the second step of the method of the invention, a therapeutic formulation containing the immunostimulatory response-reducing phosphorothioate oligonucleotide is administered to the mammal. In the third step of the method of the invention, the immune response of the mammal is monitored.

In accordance with the invention, the phosphorothioate oligonucleotide is complementary to the region of the gene being targeted and is used to modulate expression of the target gene. In unmodified form, the phosphorothioate oligonucleotide induces an immunostimulatory response. Those of skill in the art may determine whether a phosphorothioate oligonucleotide induces an immunostimulatory response in a mammal using methods such as those set forth in Examples 2 through 5 below, or by using other known methods. For example, any of the methods set forth in McIntyre, et al., supra, Messina et al., supra, Pisetsky et al, supra, Kuramoto et al., supra, or Krieg et al., supra, may be used to determine whether a phosphorothioate oligonucleotide induces an immunostimulatory response. In addition, immunostimulatory sequences, for example, those identified in Kuramoto, et al., supra, or in Krieg, et al., supra, may be identified by inspection of the sequence of the phosphorothioate oligonucleotide.

Any phosphorothioate oligonucleotide that induces an immunostimulatory response may be modified in accordance with the method of the invention. As used herein, a "phosphorothioate oligonucleotide" includes chemically synthesized polymers of about five and up to about 50, preferably from about 15 to about 30 deoxyribonucleoside and/or ribonucleoside monomers connected together or linked by at least one, and preferably more than one, 5' to 3' phosphorothioate internucleotide linkage as those terms are understood in the art.

Any immunostimulatory response-reducing modification may be introduced into the sequence or the structure of the phosphorothioate oligonucleotide in accordance with the method of the invention, so long as the target gene expression modulating activity of the oligonucleotide is maintained. For purposes of the invention, gene modulating activity occurs by virtue of complementarity of the phosphorothioate oligonucleotide to a DNA sequence within the target gene or by virtue of complementarity of the phosphorothioate oligonucleotide to an RNA sequence transcribed from the target gene. The term "complementarity" is intended to mean that the phosphorothioate oligonucleotide and the immunostimulatory response-reducing phosphorothioate oligonucleotide bind to the target nucleic acid sequence under physiological conditions, e.g., by Watson-Crick base pairing (interaction between oligonucleotide and single-stranded nucleic acid) or by Hoogsteen base pairing (interaction between oligonucleotide and double-stranded nucleic acid) or by any other means, including in the case of an oligonucleotide binding to RNA, causing pseudoknot formation. Binding by Watson-Crick or Hoogsteen base pairing under physiological conditions is measured as a practical matter by observing interference with the function of the nucleic acid sequence. It is not necessary that the phosphorothioate oligonucleotide and the corresponding Immunogenicity-reducing phosphorothioate oligonucleotide bind to the target nucleic acid with the same affinity.

The gene modulating activity of the phosphorothioate oligonucleotide is maintained in accordance with the invention when the immunostimulatory response-reducing phosphorothioate oligonucleotide is capable of changing the activity of the gene to which the phosphorothioate oligonucleotide is targeted to any degree. Preferably, an immunostimulatory response-reducing phosphorothioate oligonucleotide is capable of modulating the activity of a target gene when the target gene is expressed at a level of about 10–90% of its steady state disease expression level. More preferably, an immunostimulatory response-reducing phosphorothioate oligonucleotide is capable of modulating the activity of a target gene when the target gene is expressed at a level of less than about 50% of its steady state disease expression level. Most preferably, an immunostimulatory response-reducing phosphorothioate oligonucleotide is capable of modulating the activity of a target gene when the target gene is not detectably expressed. The steady state disease expression level of a target gene may be determined using known methods, for example, by measuring the amount of the protein encoded by the target gene in the affected mammal or in a cell or fluid derived from the affected mammal. When the target gene is present on the genome of a pathogenic organism infecting the mammal, the steady state disease expression level of a target gene may be determined by measuring the amount of the pathogenic organism shed by the infected mammal or by measuring a symptom of the infected mammal which correlates with the amount of the pathogenic organism within the mammal.

In accordance with the method of the invention, the phosphorothioate oligonucleotide may be modified to produce an immunostimulatory response-reducing phosphorothioate oligonucleotide containing a modified 3'-terminal structure, an immunostimulatory response-reducing phosphorothioate oligonucleotide containing a modified 5'-terminal structure, or an immunostimulatory response-reducing phosphorothioate oligonucleotide containing both a modified 3'-terminal structure and a modified 5'-terminal structure. In accordance with the method of the invention, a modified 3'-terminal structure comprises a chemical modification of at least one phosphorothioate nucleotide residue within six residues of the 3' terminus of the oligonucleotide. The chemical modification may occur at any site on the phosphorothioate nucleotide residue. Similarly, a modified 5'-terminal structure comprises a chemical modification of at least one phosphorothioate nucleotide residue within six residues of the 5' terminus of the oligonucleotide. The chemical modification may occur at any site on the phosphorothioate nucleotide residue.

Immunostimulatory response-reducing phosphorothioate oligonucleotides within the scope of the present invention can be prepared by art recognized methods. For example, nucleotides can be covalently linked using art recognized techniques such as phosphoramidite, H-phosphonate chemistry, or methylphosphoramidite chemistry (see, e.g., Goodchild (1990) *Bioconjugate Chem.* 2:165–187; Uhlmann et al. (1990) *Chem. Rev.* 90:543–584; Caruthers et al. (1987) *Meth. Enzymol.* 154:287–313; U.S. Pat. No. 5,149,798) which can be carried out manually or by an automated synthesizer and then processed (reviewed in Agrawal et al. (1992) *Trends Biotechnol.* 10:152–158).

The immunostimulatory response-reducing phosphorothioate oligonucleotides used in the method of the invention may also be modified in a number of ways without compromising their ability to hybridize to the target nucleic acid. For example, the oligonucleotides may contain other than phosphodiester internucleotide linkages between the 5' end of one nucleotide and the 3' end of another nucleotide in which the 5' nucleotide phosphate has been replaced with any number of chemical groups, such as a phosphorothioate. Oligonucleotides with phosphorothioate linkages can be prepared using methods well known in the field such as phosphoramidite (see, e.g., Agrawal et al. (1988) *Proc. Natl. Acad. Sci.* (USA) 85:7079–7083) or H-phosphonate (see, e.g., Froehler (1986) *Tetrahedron Lett.* 27:5575–5578) chemistry. The synthetic methods described in Bergot et al. (*J. Chromatog.* (1992) 559:35–42) can also be used. Examples of other immunostimulatory response-reducing modified chemical groups include alkylphosphonates, phosphorodithioates, alkylphosphonothioates, phosphoramidates, 2'-O-methyls, carbamates, acetamidate, carboxymethyl esters, carbonates, and phosphate triesters. Oligonucleotides with immunostimulatory response-reducing modified internucleotide linkages can be prepared according to known methods (see, e.g., Goodchild (1990) supra; Agrawal et al. (1988) supra; Uhlmann et al., supra; and Agrawal et al. (1992) supra).

Other immunostimulatory response-reducing modifications include those which include additions to the molecule at the internucleoside phosphate linkages, such as cholesteryl or diamine compounds with varying numbers of carbon residues between the two amino groups, and terminal ribose, deoxyribose and phosphate modifications which cleave, or crosslink to the opposite chains or to associated enzymes or other proteins which bind to the target genome. Examples of such immunostimulatory response-reducing modifications within the scope of the present invention include oligonucleotides having a modified base and/or sugar such as arabinose instead of ribose, or a 3', 5'-substituted oligonucleotide having a sugar which, at one or both its 3' and 5' positions is attached to a chemical group other than a hydroxyl or phosphate group (at its 3' or 5' position). Other such modifications produce capped oligonucleotides having a nuclease resistance-conferring bulky substituent at their 3' and/or 5' end(s), or having a substitution in one or both nonbridging oxygens per nucleotide, all of which modifications are capable of producing immunostimulatory response-reducing phosphorothioate oligonucleotides in accordance with the present invention. Such modifications can be at some or all of the internucleoside linkages at either or both ends of the oligonucleotide. (reviewed in Agrawal et al. (1992) supra)).

The immunostimulatory response-reducing phosphorothioate oligonucleotides are used in the method of the invention for treating pathogenic infections, for treating diseases having a genetic component such as cancer, for treating an inherited condition, and the like. Immunostimulatory response-reducing phosphorothioate oligonucleotides are used in accordance with the invention as part of a therapeutic formulation, in combination with a physiologically and/or pharmaceutically acceptable carrier. The characteristics of the carrier will depend on the route of administration. Such a formulation may contain, in addition to the immunostimulatory response-reducing phosphorothioate oligonucleotide and carrier, diluents, fillers, salts, buffers, stabilizers, solubilizers, and other materials well known in the art. The therapeutic formulation of the invention may also contain other active factors and/or agents which enhance the activity of the immunostimulatory response-reducing phosphorothioate oligonucleotides. For example, combinations of immunostimulatory response-reducing phosphorothioate oligonucleotides, each of which is directed to a different region of a pathogen genome or to a different region of an overexpressed target gene, may be used in a therapeutic formulation in accordance with the invention. Immunostimulatory response-reducing phosphorothioate oligonucleotides may be combined with other synthetic oligonucleotides within a therapeutic formulation in accordance with the invention. The therapeutic formulation may further contain other chemotherapeutic drugs for the treatment of the disease or condition of the afflicted mammal. Such additional factors and/or agents may be included in the therapeutic formulation in accordance with the method of the invention to produce a synergistic effect with the immunostimulatory response-reducing phosphorothioate oligonucleotide, or to minimize side-effects caused by the immunostimulatory response-reducing phosphorothioate oligonucleotide. Conversely, immunostimulatory response-reducing phosphorothioate oligonucleotides may be included in formulations of a particular factor and/or agent used to treat the disease or condition of the afflicted mammal, to minimize side effects of the factor and/or agent.

The therapeutic formulation used in the method of the invention may be in the form of a liposome in which the immunostimulatory response-reducing phosphorothioate oligonucleotides of the invention are combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Patent No. 4,501,728; U.S. Pat. No. 4,837,028; and U.S. Pat. No. 4,737,323. The therapeutic formulation used in the method of the invention may further include other lipid carriers, such as lipofectamine, or cyclodextrins (Zhao et al. (1995) *Antisense Res. Dev.* (in press)) and the like, which enhance delivery of oligonucleotides into cells, or such as slow release polymers.

As used herein, the term "therapeutically effective amount" means the total amount of each active component of the therapeutic formulation or method that is sufficient to show a meaningful patient benefit, i.e., a reduction in symptoms associated with the acute or chronic disease or condition being treated. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of the present invention, a therapeutically effective amount of one or more of the immunostimulatory response-reducing phosphorothioate oligonucleotides of the invention is administered to a subject afflicted with the disease or condition being treated. The immunostimulatory response-reducing phosphorothioate oligonucleotide of the invention may be administered in accordance with the method of the invention either alone or in combination with other known therapies for the disease or condition being treated. When co-administered with one or more other therapies, the immunostimulatory response-reducing phosphorothioate oligonucleotide of the invention may be administered either simultaneously with the other treatment(s), or sequentially. If administered sequentially, the attending physician will decide on the appropriate sequence of administering the immunostimulatory response-reducing phosphorothioate oligonucleotide of the invention in combination with the other therapy.

It may be desirable at times to use a mixture of different immunostumulatory-response reducing phosphorothioate oligonucleotides targeting different conserved sites within a given pathogen genome or target gene. Such a mixture of immunostimulatory-response reducing phosphorothioate oligonucleotides may be in the form of a therapeutic composition comprising at least one, and preferably two or more immunostimulatory-response reducing phosphorothioate oligonucleotides in a single therapeutic formulation (i.e., a composition comprising a physical mixture of at least two immunostimulatory-response reducing phosphorothioate oligonucleotides). These immunostimulatory-response reducing phosphorothioate oligonucleotides may have the same or different sequences. At least one, preferably two or more immunostimulatory-response reducing phosphorothioate oligonucleotides may be administered simultaneously or sequentially as a single treatment episode in the form of separate therapeutic formulations.

Administration of the immunostimulatory response-reducing phosphorothioate oligonucleotide in accordance with the method of the invention can be carried out in a variety of conventional ways, such as oral ingestion, inhalation, or cutaneous, subcutaneous, intramuscular, or intravenous injection.

When a therapeutically effective amount of immunostimulatory response-reducing phosphorothioate oligonucleotide of the invention is administered orally, the immunostimulatory response-reducing phosphorothioate oligonucleotide will be in the form of a tablet, capsule, powder, solution or elixir. When administered in tablet form, the therapeutic formulation of the invention may additionally contain a solid carrier such as a gelatin or an adjuvant. The tablet, capsule, and powder contain from about 5 to 95% immunostimulatory response-reducing phosphorothioate oligonucleotide and preferably from about 25 to 90% immunostimulatory response-reducing phosphorothioate oligonucleotide. When administered in liquid form, a liquid carrier such as water, petroleum, oils of animal or plant origin such as peanut oil, mineral oil, soybean oil, sesame oil, or immunostimulatory response-reducing phosphorothioate oils may be added. The liquid form of the therapeutic formulation may further contain physiological saline solution, dextrose or other saccharide solution, or glycols such as ethylene glycol, propylene glycol or polyethylene glycol. When administered in liquid form, the therapeutic formulation contains from about 0.5 to 90% by weight of the immunostimulatory response-reducing phosphorothioate oligonucleotide and preferably from about 1 to 50% immunostimulatory response-reducing phosphorothioate oligonucleotide.

When a therapeutically effective amount of immunostimulatory response-reducing phosphorothioate oligonucleotide used in the method of the invention is administered by intravenous, cutaneous or subcutaneous injection, the immunostimulatory response-reducing phosphorothioate oligonucleotide will be in the form of a pyrogen-free, parenterally acceptable aqueous solution. The preparation of such parenterally acceptable solutions, having due regard to pH, isotonicity, stability, and the like, is within the skill in the art. A preferred therapeutic formulation for intravenous, cutaneous, or subcutaneous injection should contain, in addition to the immunostimulatory response-reducing phosphorothioate oligonucleotide, an isotonic vehicle such as Sodium Chloride Injection, Ringer's Injection, Dextrose Injection, Dextrose and Sodium Chloride Injection, Lactated Ringer's Injection, or other vehicle as known in the art. The therapeutic formulation used in the method of the present invention may also contain stabilizers, preservatives, buffers, antioxidants, or other additives known to those of skill in the art.

The amount of immunostimulatory response-reducing phosphorothioate oligonucleotide in the therapeutic formulation used in the method of the present invention and the duration of treatment will depend upon the nature and severity of the condition being treated, on the nature of prior treatments which the patient has undergone, and on the idiosyncratic responses of the patient. Ultimately, the attending physician will decide the amount of immunostimulatory response-reducing phosphorothioate oligonucleotide with which to treat each individual patient and the duration of treatment. Initially, the attending physician will administer low doses of the immunostimulatory response-reducing phosphorothioate oligonucleotide and observe the patient's response. Larger doses of the immunostimulatory response-reducing phosphorothioate oligonucleotide may be administered until the optimal therapeutic effect is obtained for the patient, and at that point the dosage is not increased further.

The following examples illustrate the preferred modes of making and practicing the present invention, but are not meant to limit the scope of the invention since alternative methods may be used to obtain similar results.

EXAMPLE 1

PREPARATION OF OLIGONUCLEOTIDES

The oligodeoxynucleotide phosphorothioates of SEQ ID NO:1, SEQ ID NO:4, SEQ ID NO:5, SEQ ID NO:8, SEQ ID NO:9 and SEQ ID NO:10 were synthesized using an automated DNA synthesizer (Model 8700, Biosearch, Bedford, Mass.) using the β-cyanoethyl phosphoramidite approach on 10 $\mu$M scale. To generate the phosphorothioate linkages, oxidation of the intermediate phosphate linkage obtained after each coupling was carried out using 3H, 1,2-benzodithiole-3H-one-1,1-dioxide (Beaucage in *Protocols for Oligonucleotides and Analogs: Synthesis and Properties.* S. Agrawal (ed.) Humana Press, Totowa, N.J. pp. 33–62, 1993). Oligodeoxynucleotides containing phosphodiester and phosphorothioate linkages were synthesized by using the same protocol as above, except to generate phosphodiester linkages, oxidation of the intermediate phosphite linkage obtained after each coupling was carried out with standard iodine reagent (see, e.g., *Protocols for Oligonucleotides and Analogs: Synthesis and Properties.* S. Agrawal (ed.) Humana Press, Totowa, N.J. 1993). The oligonucleotide of SEQ ID NO:1 is a phosphorothioate oligonucleotide complementary to the gag region of HIV. Residues 1 to 25 of the oligonucleotide of SEQ ID NO:4 are complementary to the same portion of the gag region as is SEQ ID NO:1, and residues 22 to 33 of SEQ ID NO:4 form a stem loop at the 3'-end of the oligonucleotide. The oligonucleotide of SEQ ID NO:5 is a phosphorothioate oligonucleotide complementary to the rev region of HIV-1 which is known to stimulate the proliferation of spleen cells both in vitro and in vivo (Branda et al. (1993) *Biochem. Pharmacol.* 45:2037–2043). The oligonucleotide of SEQ ID NO:8 is a phosphorothioate oligonucleotide complementary to human p53 known to have no effect on cell proliferation (Branda, et al., supra). The oligonucleotides of SEQ ID NO:9 and SEQ ID NO:10 are 6-mer and 10-mer phosphorothioate oligonucleotides containing palindromic sequences known to induce interferon production and natural killer cell activity (Kuramoto, et al., supra).

Synthesis of the chimeric oligonucleotides of SEQ ID NO:2 and SEQ ID NO:6 was carried out on a 10 $\mu$M scale using the same instrument as above. Segments of chimeric oligonucleotide containing methylphosphonate linkages were assembled using nucleoside methylphosphonamidite (Glen Research, Sterling, Va.) followed by oxidation with 0.1 M iodine in Tetrahydrofuran/2,6-Lutidine/water, 75:25:0.25). The segment of chimeric oligonucleotide containing phosphorothioate linkage was assembled using the same procedure as described above for the oligodeoxynucleotide phosphorothioate. The deprotection of chimeric oligonucleotide was carried out in two steps. First, the CPG-bound chimeric oligonucleotide was treated with concentrated ammonium hydroxide for 1 hour at room temperature, supernate was removed and evaporated to obtain pale yellow residue. The dried residue was then treated with mixture of ethylenediamine:ethanol (1:1 I, v/v) for 6 hours and was dried again under reduced pressure. The chimeric oligonucleotides of SEQ ID NO:2 and SEQ ID NO:6 have the same sequences and lengths as SEQ ID NO:1 and SEQ ID NO:5, respectively, with substitutions of four methylphosphonate linkages at each end of the chimeric oligonucleotide.

The hybrid oligonucleotides of SEQ ID NO:3 and SEQ ID NO:7 were synthesized on 10 µM scale using the same instrument as above. The segment containing 2'-O-methylribonucleotide was synthesized using 2'-O-methylribonucleoside β-cyanoethylphosphoramidite followed by oxidation with 3H, 1,2-benzodithiole-3H-one-1, 1-dioxide (Beaucage, supra). The segment containing phosphorothioate linkages were synthesized by the same procedure as described above for oligodeoxynucleotide phosphorothioate. The hybrid oligonucleotide of SEQ ID NO:3 corresponds to the sequence and length of SEQ ID NO:1, with four 2'-O-methylribonucleotide substitutions at each end of the oligonucleotide. Similarly, the hybrid oligonucleotide of SEQ ID NO:7 corresponds to the sequence and length of SEQ ID NO:5, with four 2'-O-methylribonucleotide substitutions at each end of the oligonucleotide.

Deprotection (except for the chimeric oligonucleotides) and purification of all the oligonucleotides was carried out by the procedure described in Padmapriya et al. (1994) *Antisense Res. Dev.* 4:185–199. Purity of the oligonucleotides was checked on 20% polyacrylamide gel electrophoresis containing 7 M urea and contained more than 90% of the required length.

EXAMPLE 2

SPLENIC CELL PROLIFERATION ASSAYS

In vitro studies: Spleen was taken from a male CD1 mouse (4–5 weeks, 20–22 g, Charles River, Wilmington, Mass.). Single cell suspensions were prepared by gently mincing with frosted ends of glass slides. Cells were then cultured in RPMI complete medium [RPMI medium supplemented with 10% fetal bovine serum (FBS), 50 µM 2-mercaptoethanol (2-ME), 100 U/ml penicillin, 100 µg/ml streptomycin, 2 mM L-glutamine]. The serum was heated for 30 minutes at 56° C. for studies with phosphorothioate, chimeric, and hybrid oligonucleotides, and at 65° C. for studies with oligonucleotides containing phosphodiester segments to minimize degradation of oligonucleotides. The cells were then plated in 96-well dishes at a density of $10^6$ cells/ml in a final volume of 100 µl. Three mitogens (10 µg/ml) were used as controls for cell proliferation: Concanavalin A (Con A), a mitogen specific for T cells; pokeweed mitogen (PWM), a mitogen specific for both T and B lymphocytes; and lipopolysaccharide (LPS) which is specific for B lymphocytes.

Oligonucleotides or mitogens were added to the cells in 10 µl of TE buffer (10 mM Tris-HCl, pH 7.5, 1 mM EDTA). The cells were then set to culture at 37° C. After 44 hours, 1 µCi $^3$H-thymidine (Amersham, Arlington Heights, Ill.) was added to the culture in 20 µl of RPMI medium, and the cells were pulse-labeled for another 4 hours. The cells were then harvested by an automatic cell harvester (Skatron, Sterling, Va.) and the filters were counted by a scintillation counter.

Figure 1:
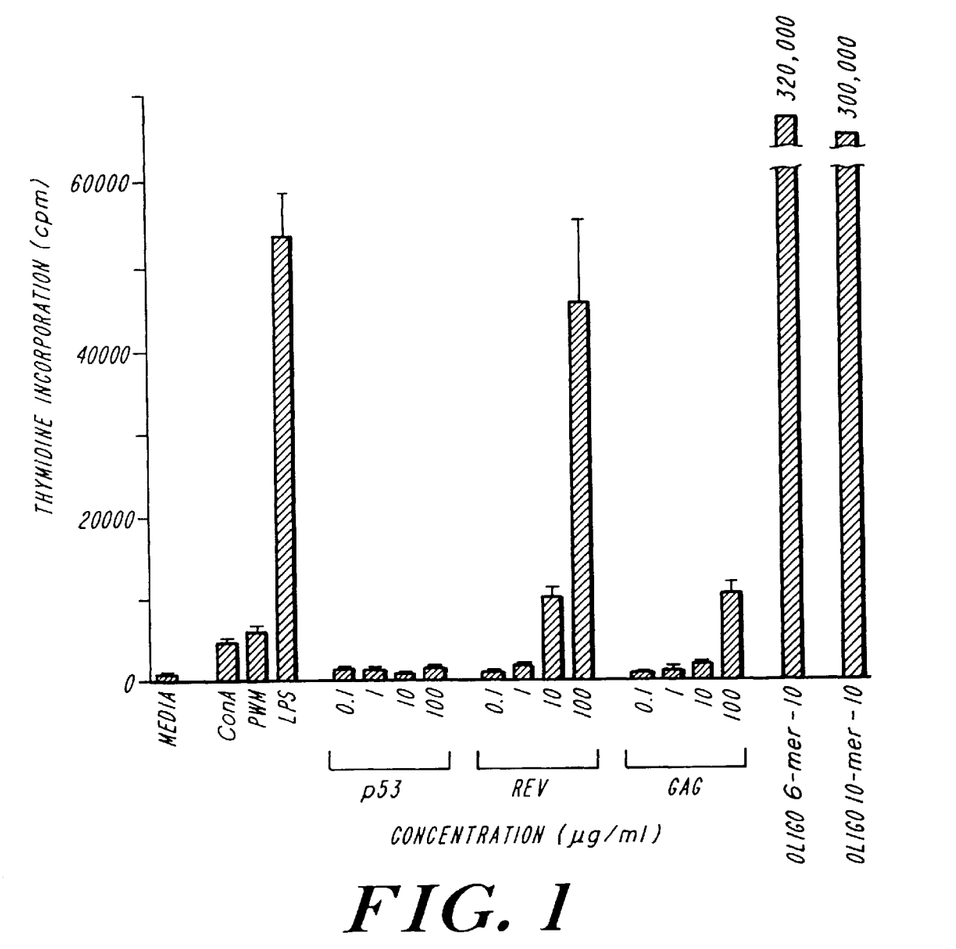
FIG. 1 shows the effect of various phosphorothioate oligonucleotides on in vitro murine splenocyte proliferation.

FIG. 1 shows that the that the rev phosphorothioate oligonucleotide of SEQ ID NO:5 and the palindrome containing phosphorothioate oligonucleotides of SEQ ID NO:9 and SEQ ID NO:10 greatly stimulated proliferation of murine splenocytes. The gag phosphorothioate oligonucleotide of SEQ ID NO:1 also induced stimulation of lymphocyte proliferation to a lesser degree. The p53 phosphorothioate oligonucleotide of SEQ ID NO:8 did not induce any significant cell proliferation at any of the concentrations studied.

Figure 2:
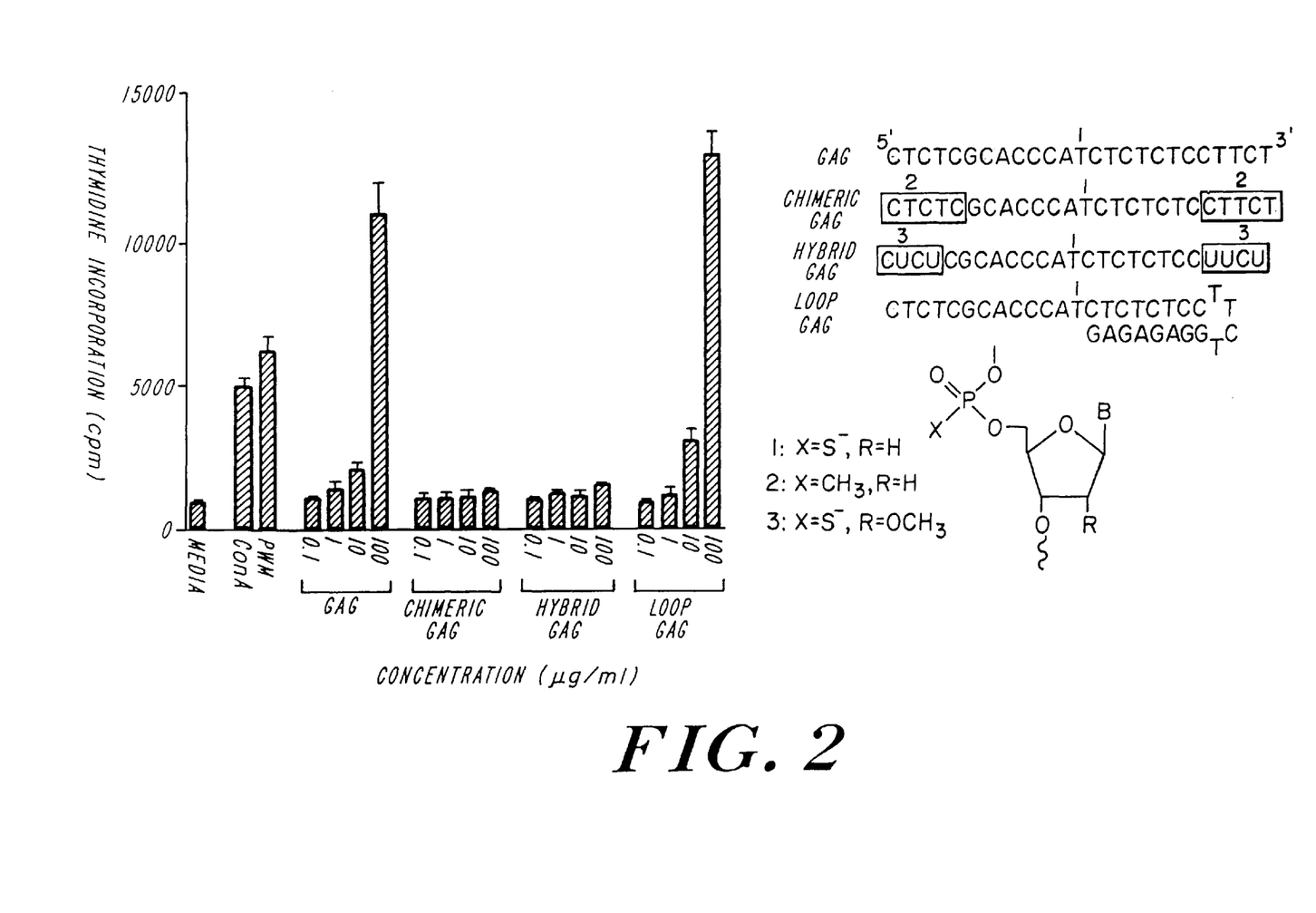
FIG. 2 shows the effect of different modified HIV-1 gag oligonucleotides on murine splenocyte proliferation.
Figure 3:
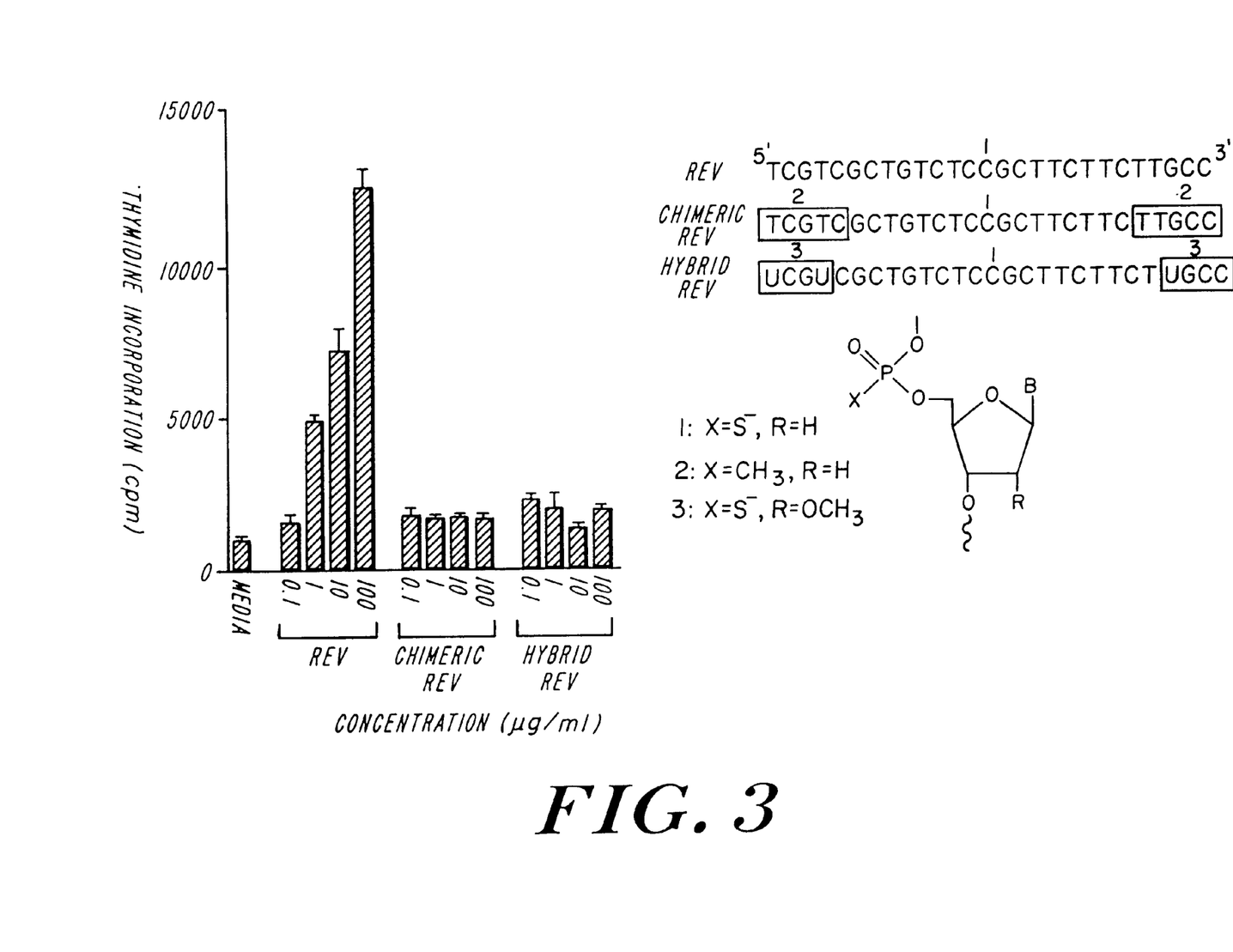
FIG. 3 shows the effect of different modified HIV-1 rev oligonucleotides on murine splenocyte proliferation.

FIG. 2 shows that the chimeric gag phosphorothioate oligonucleotide of SEQ ID NO:2 and the hybrid gag phosphorothioate oligonucleotide of SEQ ID NO:3 did not induce significant cell proliferation at any of the concentrations studied. In contrast, the stem-looped gag phosphorothioate oligonucleotide of SEQ ID NO:4 induced a similar level of cell proliferation as the oligonucleotide of SEQ ID NO:1. Similarly, FIG. 3 shows that the chimeric rev phosphorothioate oligonucleotide of SEQ ID NO:6 and the hybrid rev phosphorothioate oligonucleotide of SEQ ID NO:7 showed significantly reduced cell proliferation as compared to the rev phosphorothioate oligonucleotide of SEQ ID NO:5.

Different numbers of phosphodiester linkages were also introduced into various positions of the gag phosphorothioate oligonucleotide of SEQ ID NO:1, and such modifications significantly decreased cell proliferation as compared with the phosphorothioate oligonucleotide of SEQ ID NO:1. The gag phosphorothioate oligonucleotide SEQ ID NO:1 was also truncated from either the 5'-end or the 3'-end, and assayed for in vitro proliferation of murine splenocytes. When the length of the phosphorothioate oligonucleotide was reduced from the 5'-end, cell stimulation was length-dependent:shorter oligonucleotides produced less stimulation. Surprisingly, when the length of the oligonucleotide was reduced from the 3'-end, all lengths of the oligonucleotide showed approximately similar levels of cell proliferation as the 25-mer gag phosphorothioate oligonucleotide of SEQ ID NO:1, indicating that stimulation of murine splenocytes by this oligonucleotide is not length dependent but rather sequence or structure-dependent.

EXAMPLE 3

DEPLETION OF T CELLS

A spleen was taken from a CD1 mouse and single cell suspensions were prepared and resuspended in RPMI complete medium at a density of $10^7$ cells/ml in a volume of 1 ml. Cells were incubated with a monoclonal antibody specific for T cells, rat anti-mouse Thy 1.2 (1:100) (Gibco BRL, Gaithersburg, Md.) at 4° C. for 30 min. The cells were then washed, resuspended in RPMI medium, and incubated with Low-Tox-M Rabbit complement (1:100) (Cedarlane, Ontario, Canada) at 37° C. for 30 min. After passing through lymphocyte M (Cedarlane, Ontario, Canada) to remove destroyed T cells, cells were washed thoroughly, resuspended in RPMI complete medium and cell proliferation studies were performed as described above.

The gag phosphorothioate oligonucleotide of SEQ ID NO:1 induced cell proliferation in both the absence and presence of T cells, indicating that the stimulation observed is independent of T cells.

EXAMPLE 4

ANTIBODY PRODUCTION ASSAYS

In vitro studies: Murine splenocytes ($10^6$ cells/ml) were cultured with oligonucleotides or medium alone for 9 days in 1 ml cultures. Cell culture supernatants were then collected and assayed for IgG and IgM levels using a standard ELISA assay. Briefly, ELISA plates (96 wells) were coated with goat anti-mouse IgG or IgM (5 μg/ml) diluted in phosphate buffered saline supplemented with 0.05% sodium azide (pH 9.6) overnight at 4° C., washed 3 times with PBS-T buffer (phosphate buffered saline supplemented with 0.05% Tween 20 and 0.25% BSA), and incubated with cell culture supernatants at 37° C. for 2 hours. A standard of mouse IgG and IgM (1 mg/ml) was diluted with PBS-T buffer to provide a standard curve between 0 and 800 ng/ml. The plates were then washed 3 times with PBS-T buffer and incubated with goat anti-mouse IgG conjugated to alkaline phosphatase diluted 1:1000 with PBS-T buffer, and incubated at 37° C. for 2 hour. After 3 washes with PBS-T buffer, phosphatase substrate (pnitrophenylphosphate 1 mg/ml) in diethanolamine (75 μl) was added to the plates which were kept for 1 hr at room temperature. The colorimetric reaction was stopped by addition of 25 μl of 0.5 M sodium hydroxide. The optical density (405 nm) was measured using the reader Ceres 900 HDI (Bio-Tek Instruments, Inc). IgG and IgM levels were calculated based on the standard curve. The experiments were done in quadruplicate.

Figure 4A:
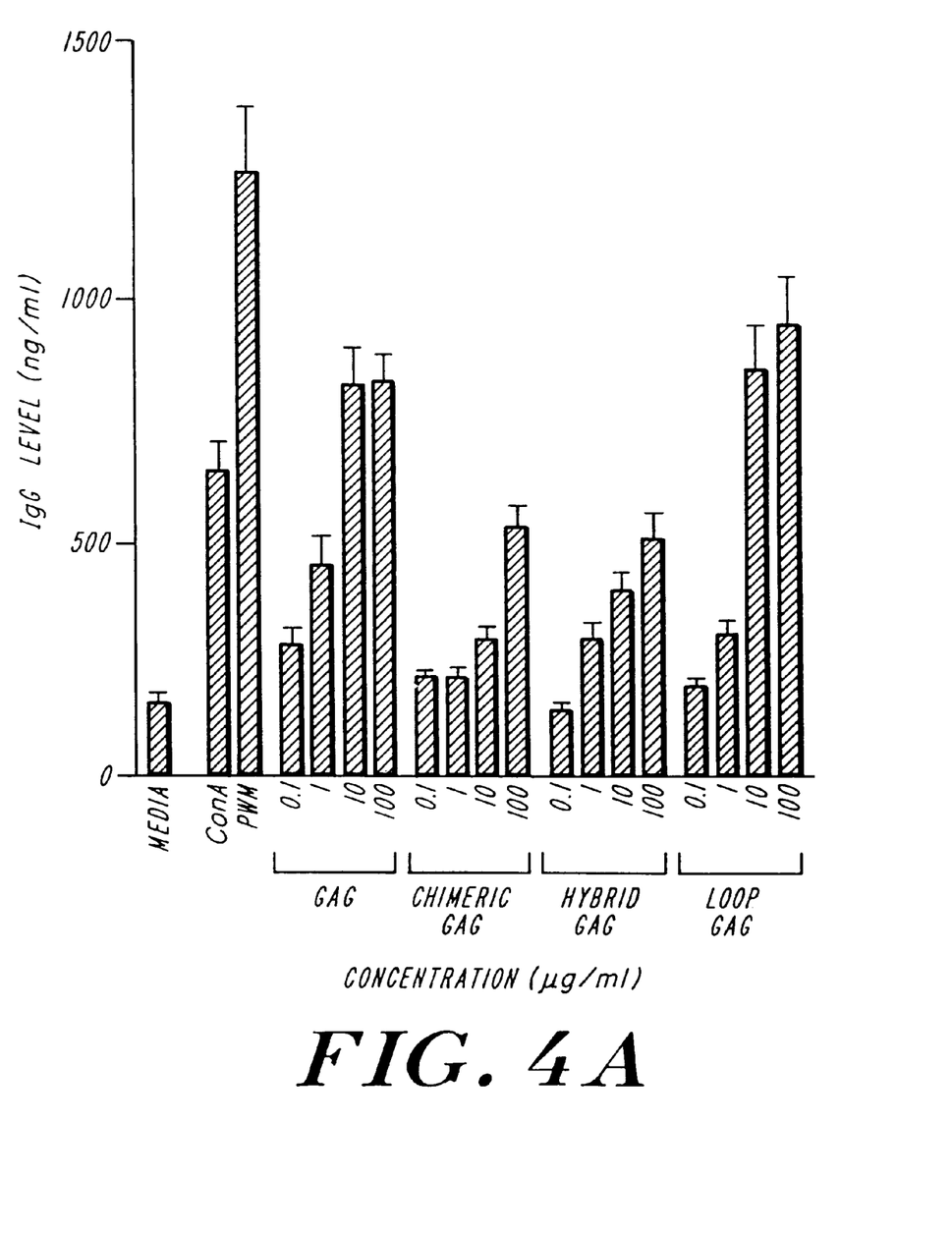
FIG. 4A shows the effect of the different modified HIV-1 gag oligonucleotides on IgG production by murine splenocytes.
Figure 4B:
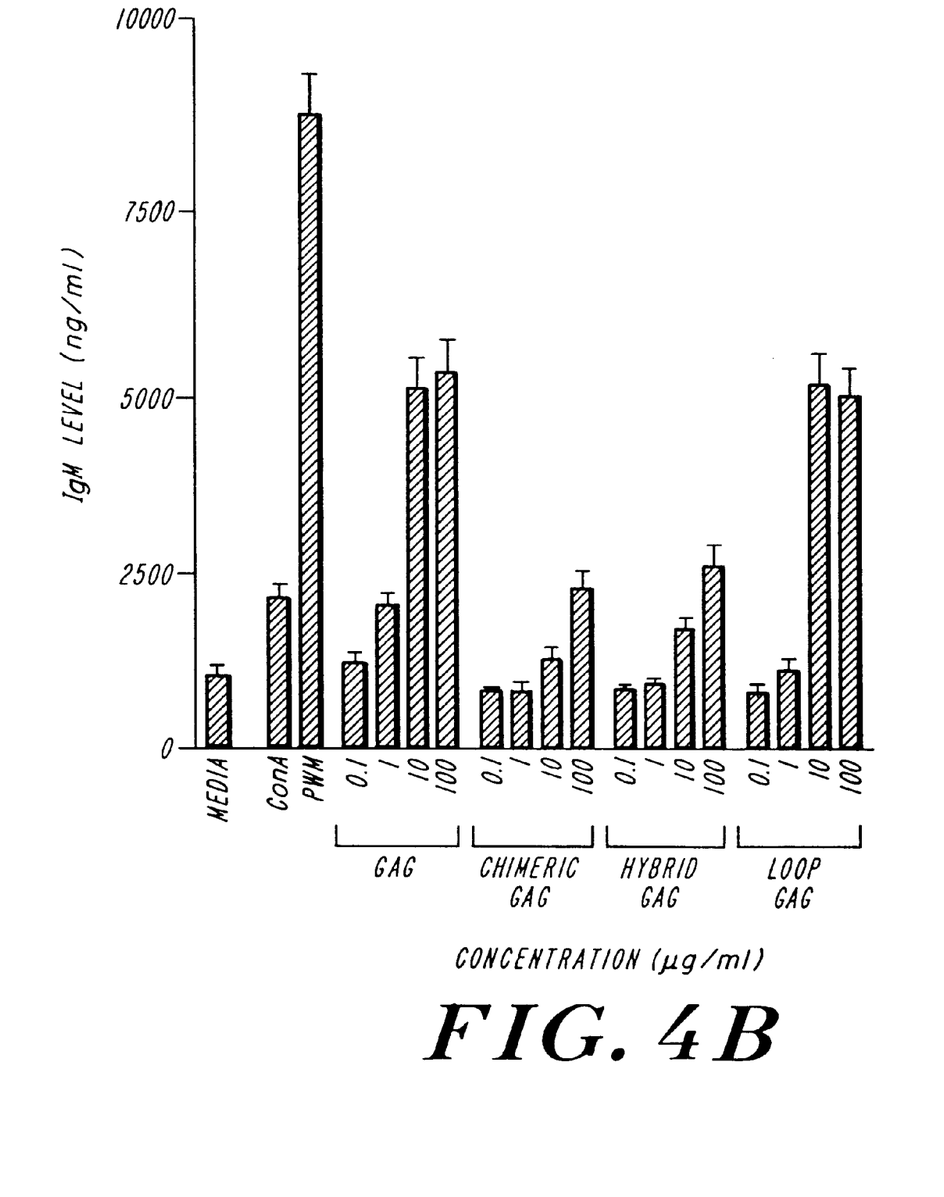
FIG. 4B shows the effect of the different modified HIV-1 gag oligonucleotides on IgM production by murine splenocytes.

FIGS. 4A and 4B show that antibody production was induced by the gag phosphorothioate oligonucleotide of SEQ ID NO:1 and the stem looped gag phosphorothioate oligonucleotide of SEQ ID NO:4 in a dose-dependent manner. FIGS. 4A and 4B also show that stimulation of antibody production by chimeric gag phosphorothioate oligonucleotide of SEQ ID NO:2 and the hybrid gag phosphorothioate oligonucleotide of SEQ ID NO:3 was significantly lower.

In vivo studies: Male CD1 mice (4–5 weeks, 20–22 g, Charles River, Wilmington, Mass.) were used in this study. The animals were fed with commercial diet and water ad lib. and were kept at the animal facility of University of Massachusetts Medical Center (Worcester, Mass.). The animals were injected intraperitoneally with 1 mg of oligonucleotide in 0.25 ml of PBS. Three animals were used for each oligonucleotide. Mice were sacrificed 48 hours later and spleen was removed and single cell suspension cell cultures were prepared and set up in culture at a density of $10^6$ cells/ml. After 24 hours of culture, the supernatants were harvested and assayed for IgG and IgM as described above. The experiments were done in triplicate.

Figure 5A:
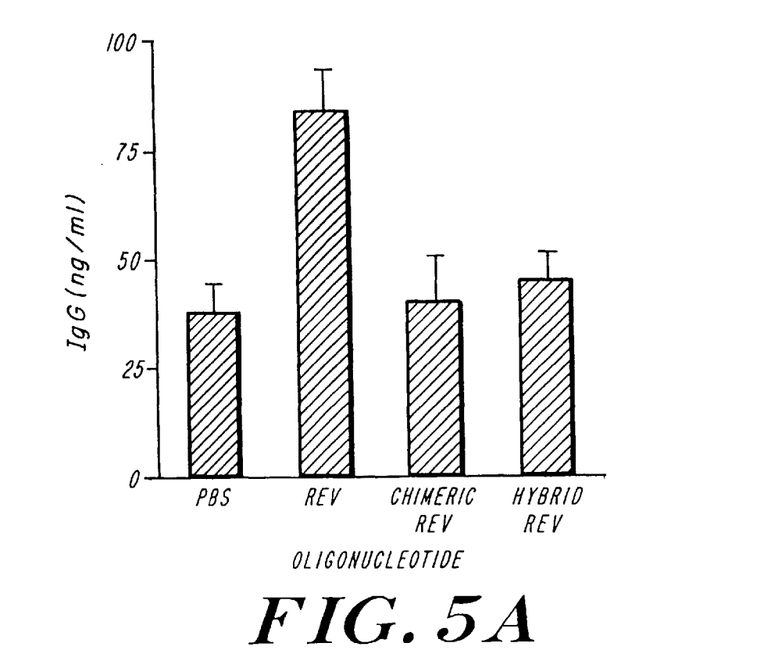
FIG. 5A shows the effect of the different modified HIV-1 rev oligonucleotides on IgG production in mice.
Figure 5B:
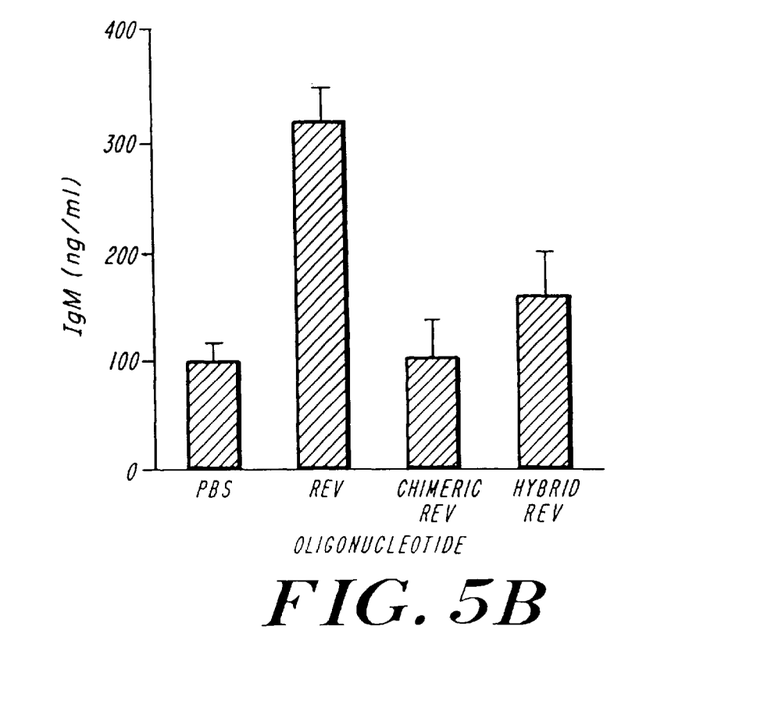
FIG. 5B shows the effect of the different modified HIV-1 rev oligonucleotides on IgM production in mice.

The gag phosphorothioate oligonucleotide of SEQ ID NO:1 and the stem looped or self-hybridizing gag phosphorothioate oligonucleotide of SEQ ID NO:4 induced about a 15% increase in spleen size as compared to mice injected with vehicle alone (PBS), while the spleens of animals treated with the rev phosphorothioate oligonucleotide of SEQ ID NO:5 were approximately doubled in size (100% increase). In contrast, the chimeric phosphorothioate oligonucleotides of SEQ ID NO:2 and SEQ ID NO:6 and the hybrid phosphorothioate oligonucleotides of SEQ ID NO:3 and SEQ ID NO:7 did not induce any significant increase in spleen weight. When the spleen cells were measured for immunoglobulin production, there was a significant increase in production of both IgG and IgM from mice injected with the rev phosphorothioate oligonucleotide of SEQ ID NO:5 (FIGS. 5A and 5B). The chimeric rev phosphorothioate oligonucleotide of SEQ ID NO:6 and the hybrid rev phosphorothioate oligonucleotide of SEQ ID NO:7 significantly minimized the antibody induction effect observed with the rev phosphorothioate oligonucleotide of SEQ ID NO:5.

EXAMPLE 5

CELL CYCLE ANALYSIS

For cell cycle analysis, the cells were cultured for 4 hours and then washed with FACS buffer (1×Hank's Balanced Salt Solution (HBSS) supplemented with 1% bovine serum albumin (BSA) and 0.1% sodium azide). The cells were fixed with 70% cold alcohol and then put on ice for 30 min. After fixation, cells were resuspended with 200 μl PBS and treated with 50 μl of RNase (10 mg/ml, DNase free) at 37° C. for 30 min. Propidium Iodide (50 μg/ml) was added to cells before flow cytometry analysis. Flow cytometric data on 10,000 viable cells were acquired in a histogram on an Epics XL flow cytometer (Coulter, Hialeah, Fla.) and data were analyzed by Epics XL, version 1.5 software and multicycle software (Phoenix Flow Systems, San Diego, Calif.) after gating on living cells by forward scatter versus side scatter and excluding doublets. The experiments were done in triplicate.

The results of the cell cycle analysis are set forth in Tables 1 and 2, in which the results are presented as % of cells±standard deviation of a quadruplicate experiment

TABLE 1

| SAMPLE | % CELLS IN G1 | % CELLS IN S/G2 |
| --- | --- | --- |
| PBS | 88.3 ± 0.25 | 11.7 ± 0.20 |
| SEQ ID NO: 1 (gag) | 86.9 ± 0.39 | 13.1 ± 0.38 |
| SEQ ID NO: 2 (gag chimeric) | 88.4 ± 0.71 | 11.3 ± 0.29 |
| SEQ ID NO: 3 (gag hybrid) | 88.3 ± 0.21 | 11.8 ± 0.21 |
| SEQ ID NO: 3 (gag loop) | 87.7 ± 2.59 | 12.7 ± 1.96 |

TABLE 2

| SAMPLE | % CELLS IN G1 | % CELLS IN S/G2 |
| --- | --- | --- |
| PBS | 85.4 ± 0.36 | 14.6 ± 0.32 |
| SEQ ID NO: 1 (rev) | 81.3 ± 0.36 | 18.7 ± 0.45 |
| SEQ ID NO: 2 (rev chimeric) | 85.9 ± 1.90 | 14.1 ± 1.90 |
| SEQ ID NO: 3 (rev hybrid) | 85.7 ± 0.46 | 14.3 ± 0.46 |

The cell cycle studies show that after staining fixed spleen cells with propidium iodide, the percentage of cells in the S/G2 phases from mice treated with the gag phosphorothioate oligonucleotide of SEQ ID NO:1, and the stem looped gag phosphorothioate oligonucleotide of SEQ ID NO:4, increased by about 13%, as compared with untreated mice. The rev phosphorothioate oligonucleotide of SEQ ID NO:5 induced an approximate 30% increase in the percentage of cells in S/G2 phases of the cell cycle, compared to the vehicle alone. The chimeric phosphorothioate oligonucleotides of SEQ ID NO:2 and SEQ ID NO:6 and the hybrid phosphorothioate oligonucleotides of SEQ ID NO:3 and SEQ ID NO:7 showed no significant increase in cycling cells, confirming the results observed in vitro.

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method of reducing an immunostimulatory response of a mammal to a phosphorothioate oligonucleotide which comprises:

a. modifying at least one chemical structure in the phosphorothioate oligonucleotide to produce an immunostimulatory response-reducing phosphorothioate oligonudeotide, wherein the chemical modification is selected from the group consisting of introducing non-phosphorothioate linkages into the oligonucleotide, altering the degree of substitution with phosphorothioate internucleotide linkages in the oligonucleotide, substituting ribonucleotides for deoxyribonucleotides on the sugar backbone, modifying the terminal ribose, deoxyribose, and phosphate groups to cleave or crosslink to the opposite chains or to associated enzymes or other proteins which bind to the target genome, adding a cholesteryl or diamine compound to the internucleotide linkage group, modifying the sugar to attach at one or both of its 3' and 5' positions a chemical group other than hydroxyl or phosphate, capping the oligonucleotide with a nuclease resistance-conferring bulky substituent at one or both of the 3' and 5' ends, and substituting one or both nonbridging oxygens in a nucleotide;

b. administering a therapeutic formulation containing the immunostimulatory response-reducing phosphorothioate oligonucleotide to the mammal; and c. monitoring the immune response of the mammal for a reduced immunostimulatory response.

2. The method of claim 1, wherein the immunostimulatory response-reducing phosphorothioate oligonucleotide has a modified 3'-terminal structure.

3. The method of claim 2, wherein the modified 3'-terminal structure comprises a substitution of at least one methylphosphonate internucleotide linkage for at least one phosphorothioate internucleotide linkage of the oligonucleotide.

4. The method of claim 2, wherein the modified 3'-terminal structure comprises a substitution of at least one ribonucleotide for at least one deoxyribonucleotide.

5. The method of claim 2, wherein the modified 3'-terminal structure comprises a substitution of at least-one internucleotide linkage to disrupt a sequence which induces an immunostimulatory response.

6. The method of claim 1, wherein the immunostimulatory response-reducing phosphorothioate oligonucleotide has a modified 5'-terminal structure.

7. The method of claim 6, wherein the modified 5'-terminal structure comprises a substitution of at least one methylphosphonate internucleotide linkage for at least one phosphorothioate internucleotide linkage of the oligonucleotide.

8. The method of claim 6, wherein the modified 5'-terminal structure comprises a substitution of at least one ribonucleotide for at least one deoxyribonucleotide.

9. The method of claim 6, wherein the modified 5'-terminal structure comprises a substitution of at least one nucleotide for another different nucleotide to disrupt a nucleotide sequence which induces an immunostimulatory response.

10. The method of claim 1, wherein the immunostimulatory response-reducing phosphorothioate oligonucleotide has a modified 3'-terminal structure and a modified 5'-terminal structure.

11. The method of claim 10, wherein the modified 3'-terminal structure comprises a substitution of at least one methylphosphonate internucleotide linkage for at least one phosphorothioate internucleotide linkage of the oligonucleotide.

12. The method of claim 10, wherein the modified 3'-terminal structure comprises a substitution of at least one ribonucleotide for at least one deoxyribonucleotide.

13. The method of claim 10, wherein the modified 3'-terminal structure comprises a substitution of at least one nucleotide for another different nucleotide to disrupt a nucleotide sequence which induces an immunostimulatory response.

14. The method of claim 10, wherein the modified 5'-terminal structure comprises a substitution of at least one methylphosphonate internucleotide linkage for at least one phosphorothioate internucleotide linkage of the oligonucleotide.

15. The method of claim 10, wherein the modified 5'-terminal structure comprises a substitution of at least one ribonucleotide for at least one deoxyribonucleotide.

16. The method of claim 10, wherein the modified 5'-terminal structure comprises a substitution of at least one nucleotide for another different nucleotide to disrupt a nucleotide sequence which induces an immunostimulatory response.

17. The method of claim 10, wherein the modified 3'-terminal structure comprises a substitution of at least one methylphosphonate internucleotide linkage for at least one phosphorothioate internucleotide linkage of the oligonucleotide and the modified 5'-terminal structure comprises a substitution of at least one methylphosphonate internucleotide linkage for at least one phosphorothioate internucleotide linkage of the oligonucleotide.

18. The method of claim 10, wherein the modified 3'-terminal structure comprises a substitution of at least one ribonucleotide for at least one deoxyribonucleotide, and the modified 5'-terminal structure comprises a substitution of at least one ribonucleotide for at least one deoxyribonucleotide.

19. The method of claim 10, wherein the modified 3'-terminal structure comprises a substitution of at least one nucleotide to disrupt a nucleotide sequence which induces an immunostimulatory response, and the modified 5'-terminal structure comprises a substitution of at least one nucleotide to disrupt a nucleotide sequence which induces an immunostimulatory response.

* * * * *